(12) United States Patent
Aduana, Jr. et al.

(10) Patent No.: US 6,796,953 B2
(45) Date of Patent: Sep. 28, 2004

(54) CERVICAL TRACTION DEVICE

(76) Inventors: Efren B. Aduana, Jr., 3609 S. Francisco Ave., Chicago, IL (US) 60632; Efren M. Aduana, 3609 S. Francisco Ave., Chicago, IL (US) 60632

( * ) Notice: Subject to any disclaimer, the term of this patent is extended or adjusted under 35 U.S.C. 154(b) by 123 days.

(21) Appl. No.: 10/317,189

(22) Filed: Dec. 12, 2002

(65) Prior Publication Data

US 2004/0133140 A1 Jul. 8, 2004

(51) Int. Cl.[7] ................................................. A61F 5/00
(52) U.S. Cl. ........................................... 602/32; 602/36
(58) Field of Search ...................... 602/32–40; 128/845, 128/869, 870

(56) References Cited

U.S. PATENT DOCUMENTS

| | | | |
|---|---|---|---|
| 2,822,805 A | * | 2/1958 | Hill |
| 3,629,581 A | | 12/1971 | Smith |
| 4,010,744 A | * | 3/1977 | Boyen ........................... 128/75 |
| 4,383,524 A | | 5/1983 | Boger |
| 4,539,979 A | * | 9/1985 | Bremer .......................... 128/75 |
| 4,674,483 A | | 6/1987 | Frederick |
| 5,342,290 A | * | 8/1994 | Schuellein .................... 602/36 |
| 5,370,605 A | | 12/1994 | Weed |
| 5,788,659 A | * | 8/1998 | Haas ............................ 602/36 |
| 5,875,781 A | | 3/1999 | Klaus |
| 6,708,693 B1 | * | 3/2004 | Choy ........................... 128/845 |

\* cited by examiner

Primary Examiner—Michael A. Brown
(74) Attorney, Agent, or Firm—Richard C. Litman

(57) ABSTRACT

The present invention relates to a traction device for applying a caudal force to the shoulders of a patient who is in the supine position on an examination table. The device causes the patient's shoulders to be drawn downward to allow accurate lateral radiographs of the complete cervical spine. The device comprises two shoulder pads, a tension strap assembly, and a rigid traction applicator, the tension straps extending over the foot end of the examination table and the traction applicator depending therefrom. The tension strap assembly extends between and connects the shoulder pads and the traction applicator. The shoulder pads are positioned over the acromioclavicular joints of the patient's shoulders.

17 Claims, 9 Drawing Sheets

CERVICAL TRACTION DEVICE

BACKGROUND OF THE INVENTION

1. Field of the Invention

The present invention relates to a traction device for positioning a patient for an x-ray and, more particularly, to a cervical traction device for obtaining a lateral radiograph of the cervico-thoracic spine, including C-7 and T-1.

2. Description of the Related Art

Frequently in hospital emergency rooms, as well as in other non-emergency clinical settings, various injuries necessitate radiographs to be taken of the cervical spine. However, accurate lateral radiographs of the cervical or neck region of the vertebral column are difficult to obtain because of interference from the shoulders. As such, some injuries to the vertebrae go undetected.

To obtain lateral radiographs of the cervical spine, it is common practice for the radiographer to have an assistant depress the shoulders of the patient caudally. Typically, this is done by having the assistant stand at the foot of the bed, grasp the patient's wrists, and pull the patient's wrists toward the foot of the bed. When the patient's shoulders are depressed below the level of the C7-T1 junction, the radiographer takes the X-ray of. the cervical spine. Often the patient is pulled towards a sitting position during this procedure. For patients who are severely injured or unconscious, this process can be painful and even dangerous. In addition, the assistant risks exposure to radiation.

Alternative methods for obtaining radiographs of this region of the body also suffer significant drawbacks.

U.S. Pat. No. 4,383,524, issued May 17, 1983 to D. Boger, discloses a traction aid for lowering the shoulders during lateral cervical spine radiographic procedures. The device employs a pair of wrist cuffs joined by an adjustable loop which extends around the underside of the feet of a patient. The adjustable loop is formed by a flexible, inextensible strap having opposing ends joined by hook and loop fastening material below the patient's feet. The patient flexes his knees when the loop is formed so that the loop is shorter than the distance between the patient's wrists and feet when the patient's legs are extended. Straightening the knees and extending the feet tensions the patient's arms and depresses the patient's shoulders, allowing improved exposure of the sixth and seventh vertebrae to lateral X-ray procedures. An alternative embodiment, shown in FIGS. 7, 10 and 11, includes a shoulder harness attached to the device at the wrist straps by hook and loop fastening material. One drawback with this invention is that patients who do not have the ability to straighten their knees and extend their feet, e.g., patient's who have suffered trauma and are unconscious, will not be able to utilize this device.

U.S. Pat. No. 5,370,605, issued Dec. 6, 1994 to A. Weed, discloses a cervical visualization harness for use in applying traction to sedated and/or anesthetized patients. The cervical visualization harness includes a body portion and a pair of straps which extend from the body portion up over the shoulders of the patient and down the patient's body to appropriate points either between the patient's feet or to either side of the foot of the operating room table to achieve a desired position of the patient's shoulders. The ends of the straps are secured to portions of the operating room table by hook and loop fastening material. This device constrains the patient's shoulders for a period before and after the X-ray is actually taken, thereby causing prolonged discomfort for the patient.

U.S. Pat. No. 5,875,781, issued Mar. 2, 1999 to D. Klaus, discloses a system for applying force caudally to the shoulders of a patient laying flat on a hospital table for purposes of taking x-rays of the neck area of the patient. This system includes a shoulder harness having a band near the shoulders with straps attached to the band. Each strap extends longitudinally across the body of the patient and engages opposite edges of the examining table. The straps are directed downward by means of pulleys and have weights hanging at their ends.

Other devices for obtaining radiographs of the cervical spine include U.S. Pat. No. 3,629,581, issued Dec. 21, 1971 to J. Smith (device for facilitating unobstructed X-ray examination of cervical spine having support with vertically disposed foot rest); and U.S. Pat. No. 4,674,483, issued Jun. 23, 1997 to P. Frederick (shoulder retraction apparatus for use on a patient).

None of the above inventions and patents, taken either singly or in combination, is seen to describe the instant invention as claimed. Thus, a cervical traction device solving the aforementioned problems is desired.

SUMMARY OF THE INVENTION

The present invention relates to a traction device for applying a caudal force to the shoulders of a patient who is in the supine position on an examination table. The device causes the patient's shoulders to be drawn downward to allow accurate lateral radiographs of the complete cervical spine. The device comprises two shoulder pads, a tension strap assembly, and a traction applicator. The tension strap assembly extends between and connects the shoulder pads and the traction applicator. The shoulder pads are positioned over the patient's shoulders.

When the device is properly positioned on a patient who is lying on an examination table, a portion of the tension straps extend longitudinally along either side of the patient while the remaining portion of the tension straps depend downwardly from the edge of the table and carry the traction applicator above the floor surface. A radiographer's assistant applies downward pressure to the traction applicator, so that traction is provided to depress the patient's shoulders caudally.

Accordingly, it is a principal object of the invention to provide a cervical traction device which facilitates positioning a patient for a lateral x-ray view of the cervical spine.

It is another object of the invention to provide a cervical device which can be employed without requiring any effort from a patient.

It is a further object of the invention to provide a cervical traction device which can be employed quickly and easily.

Still another object of the invention is to provide a cervical traction device which minimizes radiation exposure to both the patient and a radiographer's assistant performing the procedure.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
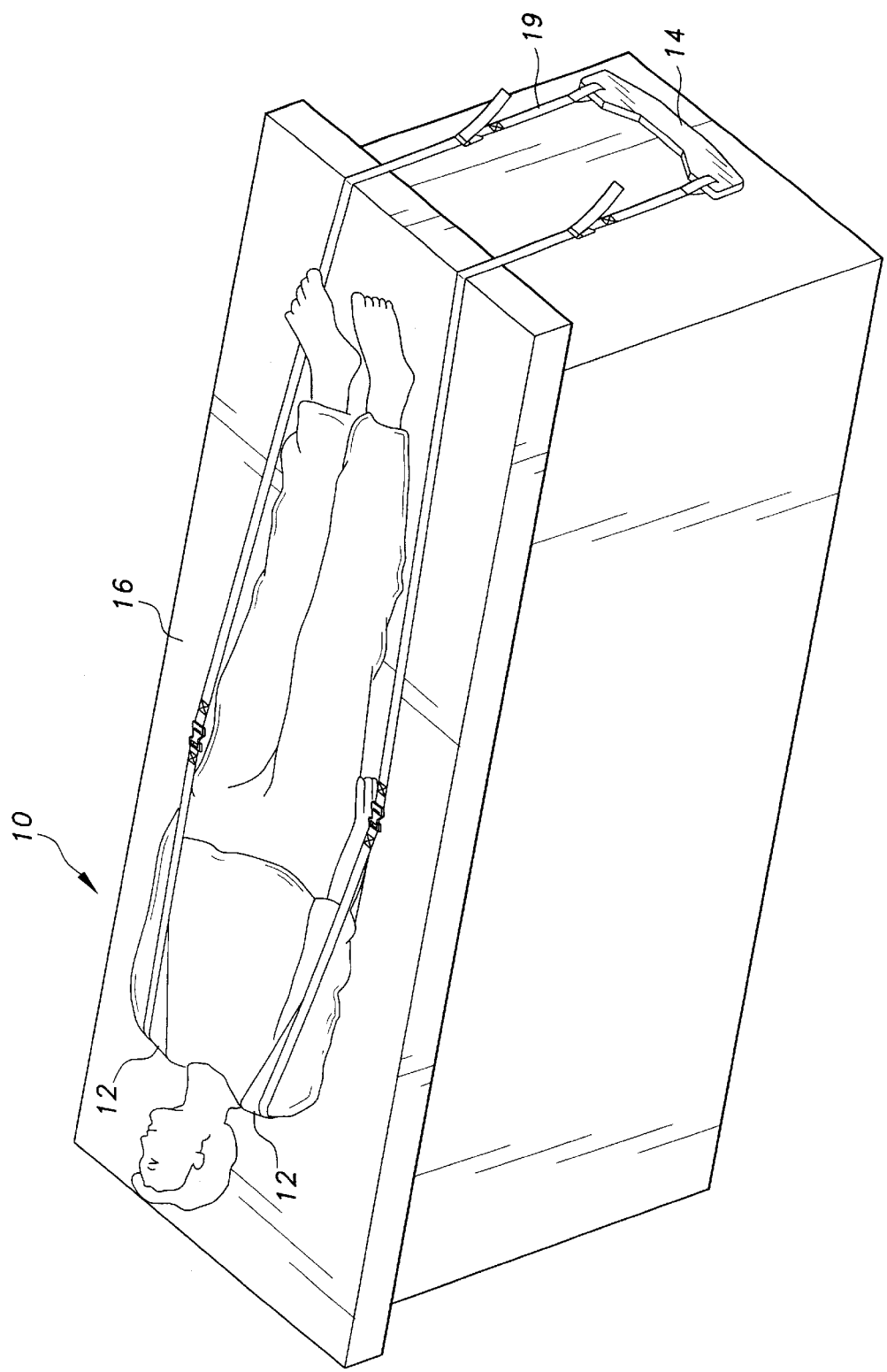
FIG. 1 is an environmental, perspective view of a cervical traction device properly positioned on a patient according to the present invention.

The present invention relates to a cervical traction device 10 for applying a caudal force to the shoulders of a patient lying in the supine position on a horizontal support surface, such as an examination table, as shown in FIG. 1.

In one embodiment, the traction device 10 comprises a pair of shoulder pads 12, a traction applicator 14, a tension strap assembly 16, and traction applicator straps 19. The tension strap assembly 16 and the traction applicator straps 19 are joined together to extend between and connect the shoulder pads 12 and the traction applicator 14. As is shown, the shoulder pads 12 are positioned over the shoulders of the patient, proximate the acromioclavicular joints. When pressure is applied to the traction applicator 14, the tension strap assembly 16 draws the patient's shoulders down caudally to expose the lower portion of the cervical spine for a lateral X-ray view of the cervical spine.

Figure 2:
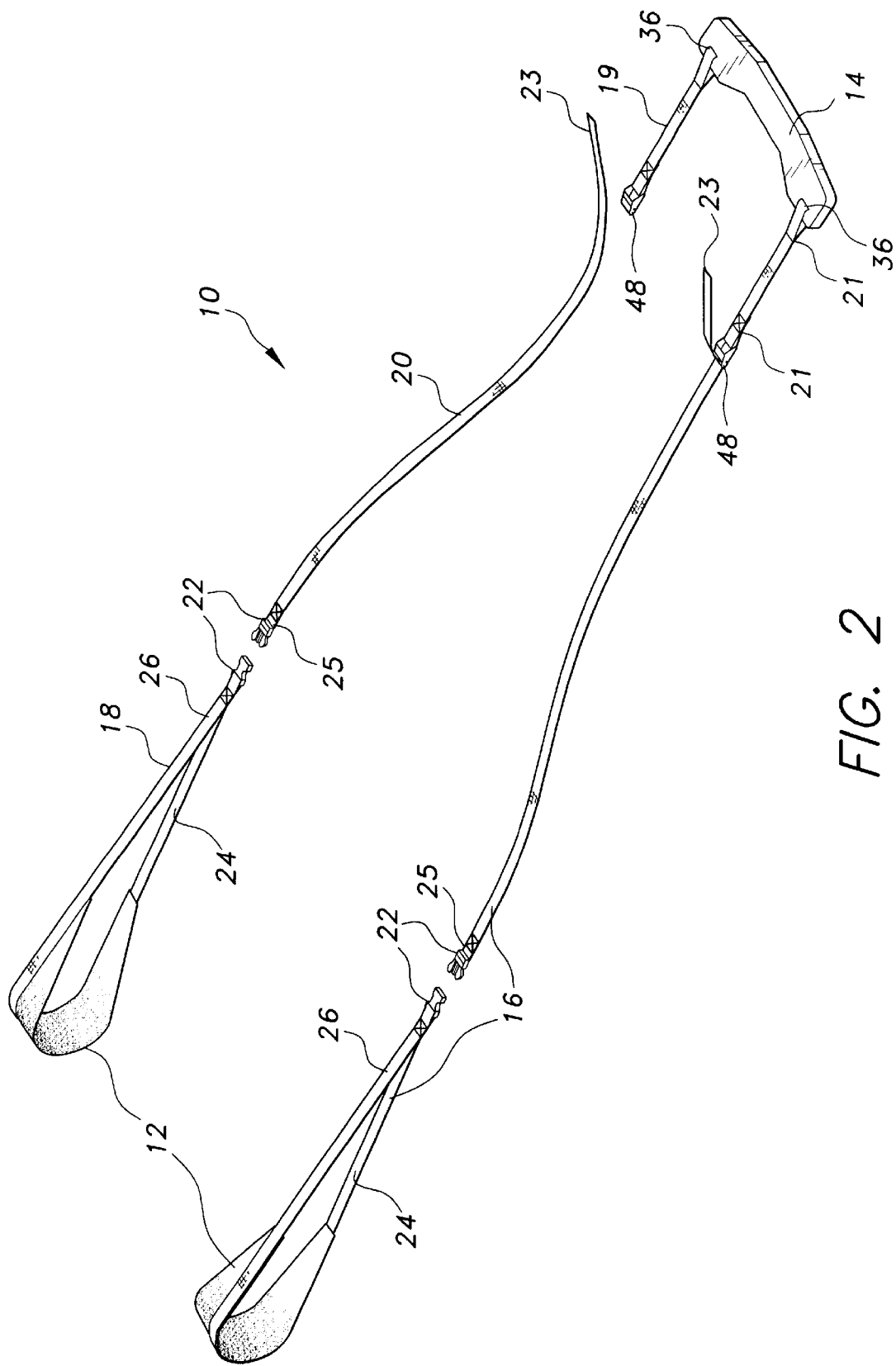
FIG. 2 is a perspective side view of a cervical traction device with traction applicator straps according to the present invention.

As shown in FIG. 2, the tension strap assembly 16 is comprised of a pair of looped tension straps 18 and a pair of straight tension straps 20. The straight straps 20 have opposing first and second ends 23 and 25. Preferably, the looped straps 18 and the straight straps 20 are releasably attached to one another by a releasable fastener portion 22 as shown in FIG. 2. Releasable fastener portion 22 includes, but is not limited to buckles, spring closure hooks, in-line slide fasteners, quick release buckles having resilient prongs engaging mating receptacles as shown in FIG. 2, and cam-action and hook-and-loop fasteners. Alternatively, however, the looped straps 18 and the straight straps 20 may be made from one piece (not shown). The looped straps 18 and the straight straps 20 of the tension strap assembly 16 can be made from nylon webbing or any other suitable flexible, inelastic material.

Figure 3:
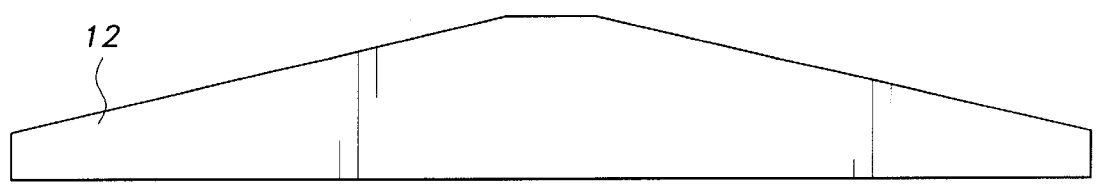
FIG. 3 is a perspective view of a shoulder pad according to the present invention.

The looped straps 18 have inner and outer loop surfaces, 24 and 26. The shoulder pads 12 are attached to the inner surface 24 of the looped straps 18. The shoulder pads 12 may be attached by adhesives, hook-and-loop fasteners, or any other suitable means. The shoulder pads 12 can be of any suitable shape and can be made from any flexible, but resilient material having a coefficient of friction which will resist slippage on clothes and skin. Preferably, the shoulder pads 12 are substantially triangular, as shown in FIG. 3, and made from rubber or synthetic rubber materials.

Figure 4:
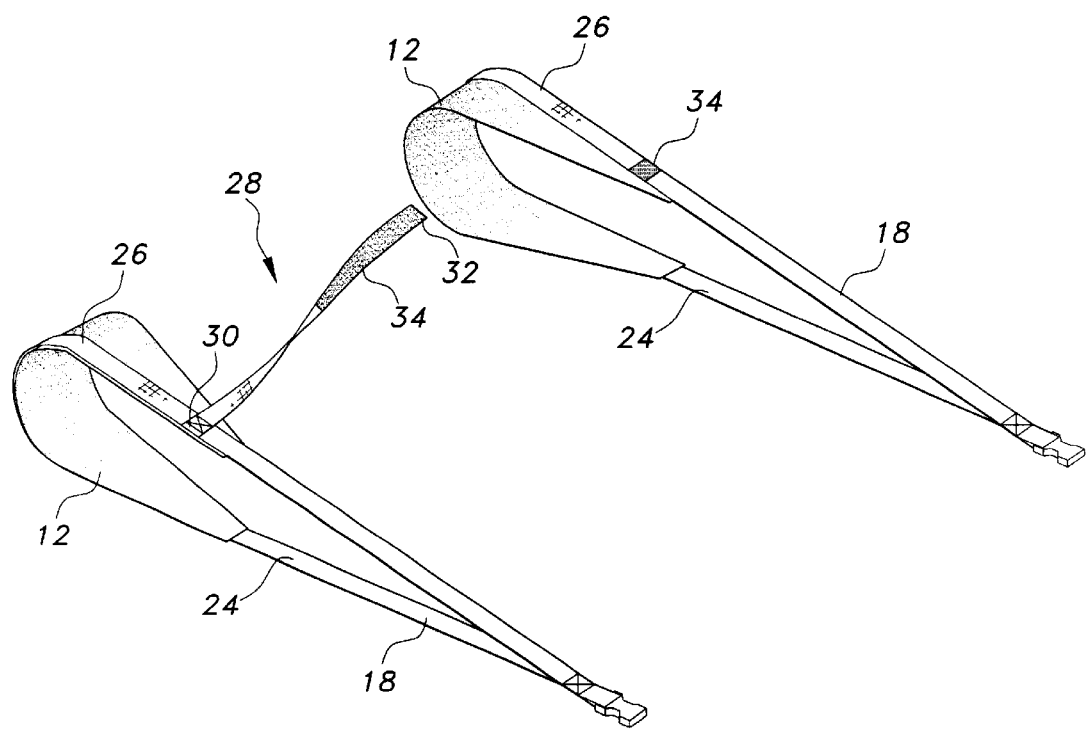
FIG. 4 is a perspective side view of looped tension straps and a fastening strap according to the present invention.

As shown in FIG. 4, a fastening strap 28 having first and second fastening ends 30 and 32 may optionally be transversely attached between the two loops 18 to hold the looped straps 18 on the patient's shoulders. Preferably, the first end 30 is stitched or otherwise attached to one looped strap 18, while the second end 32 is attached to the remaining looped strap 18 with mating patches of hook-and-loop fastening material 34.

Figure 5:
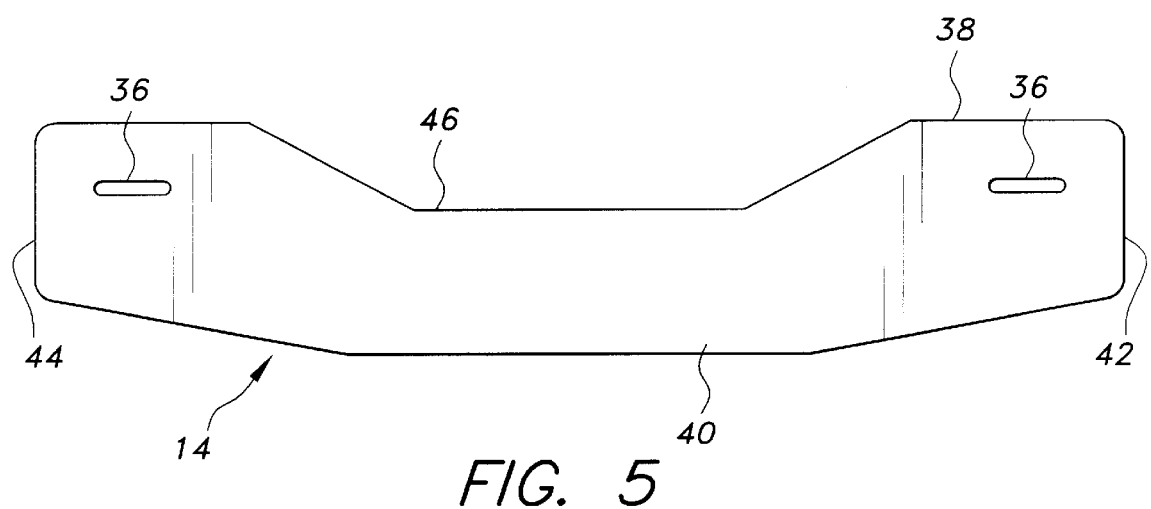
FIG. 5 is a perspective front view of a traction applicator according to the present invention.

The traction applicator 14 is rigid and can be made from wood, molded plastic, aluminum, or any other suitable material. As is shown in FIG. 5, the traction applicator 14 is substantially rectangular, having, an opposing top end 38 and bottom end 40 which are connected by parallel, opposing right side 42 and left side 44. A recess 46 is positioned at the horizontal center of the top end 38, the recess, 46 being dimensioned and configured to accommodate the width of a foot so that an assistant may place his foot in the recess 38 and step downward to depress the patient's shoulders caudally. The traction applicator also has a pair of strap slots 36 proximate opposing right and left sides 42 and 44.

The traction applicator 14 may be connected to the straight tension straps 20 by any suitable means. Referring back to FIG. 2, it can be seen that the traction applicator straps 19 can be looped through the strap slots 36 in the traction applicator 14 and secured by attaching overlapping positions of the same traction applicator straps 19 at various attachment points 21 by stitching or other suitable means. Strap engaging brackets 48 can then be used to attach the straight tension straps 20 to the traction applicator straps 19. Suitable strap engaging brackets 48 include cam-action fasteners or other devices which allow for length adjustment of the straight straps 20.

Referring back to FIG. 1, it can be seen that when the shoulder pads 12 are properly positioned over the patient's shoulders, a portion of the straight tension straps 20 extend longitudinally along either side of the patient while the remaining portion of the straight tension straps 20 depend downwardly from the edge of the table and carry the traction applicator 14 above the floor surface.

Figure 6:
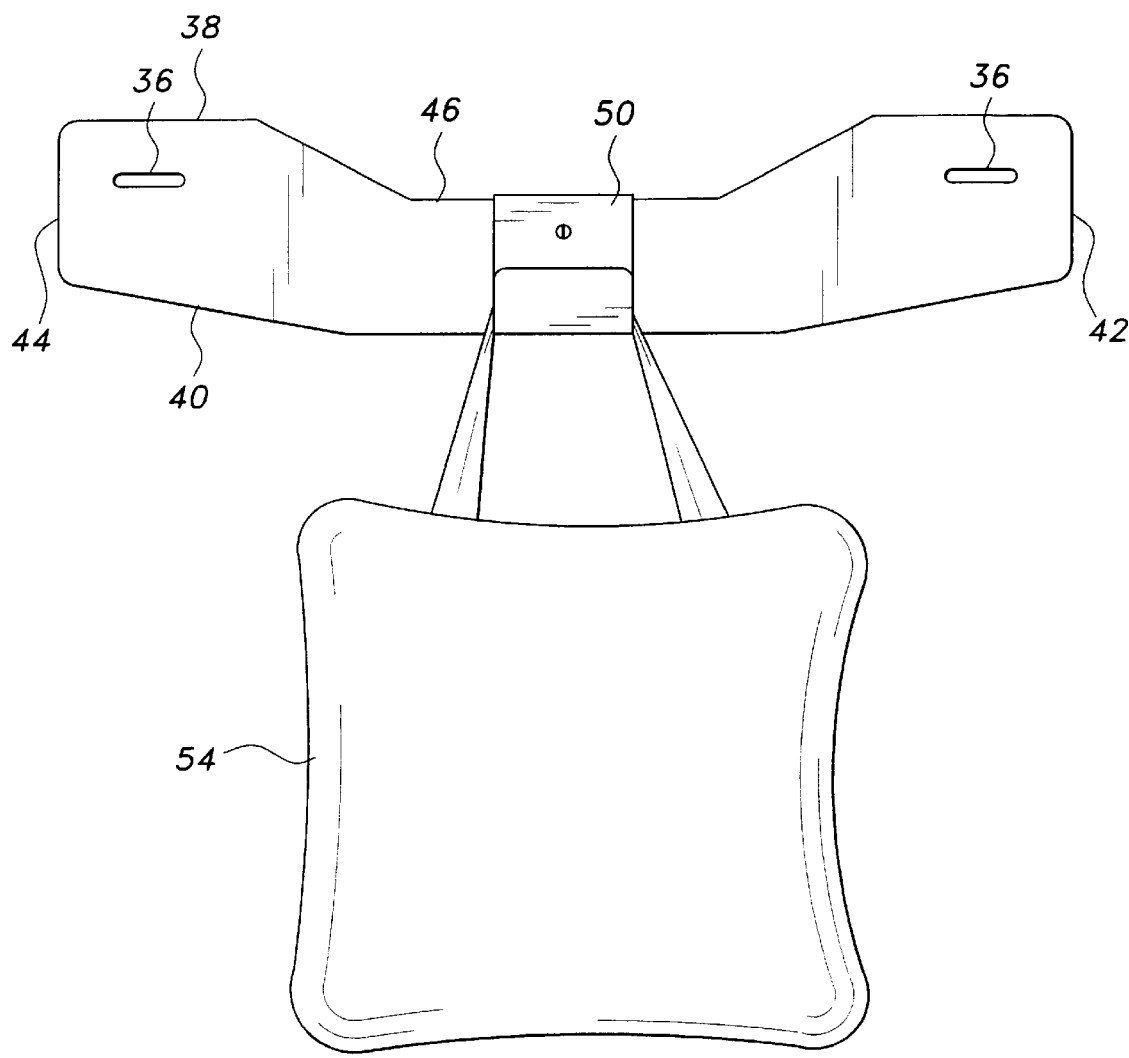
FIG. 6 is a perspective front view of a sandbag attached to a traction applicator according to the present invention.
Figure 7:
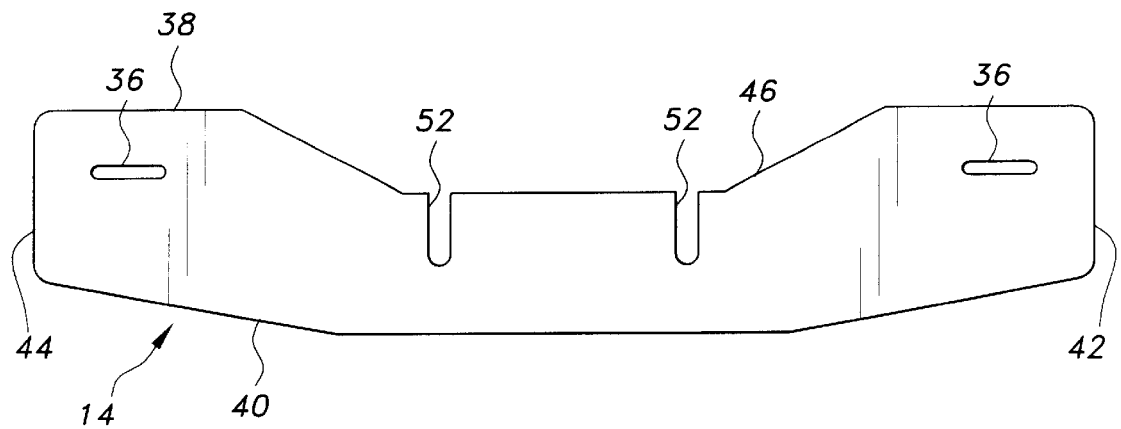
FIG. 7 is a perspective front view of a traction applicator with indentations according to the present invention.
Figure 8:
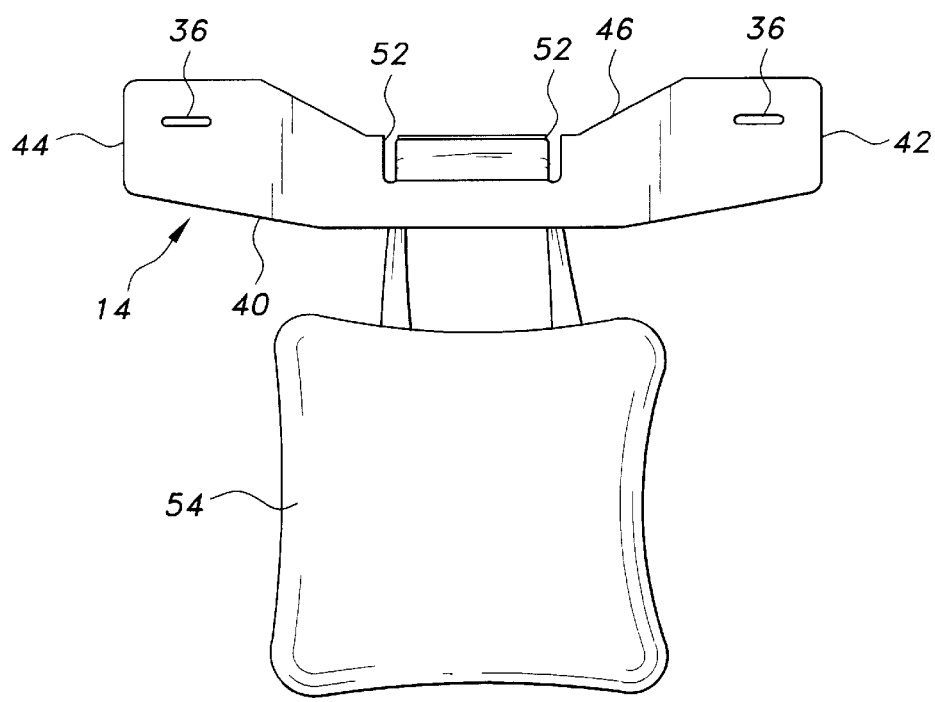
FIG. 8 is a perspective front view of a sandbag attached to a traction applicator with indentations according to the present invention.

The traction applicator can be employed in several ways to provide traction to the shoulders. Preferably, the depression 46 in the traction applicator provides a platform upon which a doctor, nurse, or other person assisting the radiologist or radiology technician may place one foot and apply traction evenly to both of the patient's shoulders. Alternatively, as depicted in FIGS. 6–8, a sandbag 54 can be used to provide traction. A bracket 50 from which to hang the sandbag 54 may be positioned in the depression 46 and affixed to the traction applicator 14, as shown in FIG. 6, or indentations 52 can be formed at the top end 38 of the traction applicator 14 to define a lug from which to hang the sandbag 54, as depicted in FIGS. 7–8.

Figure 9:
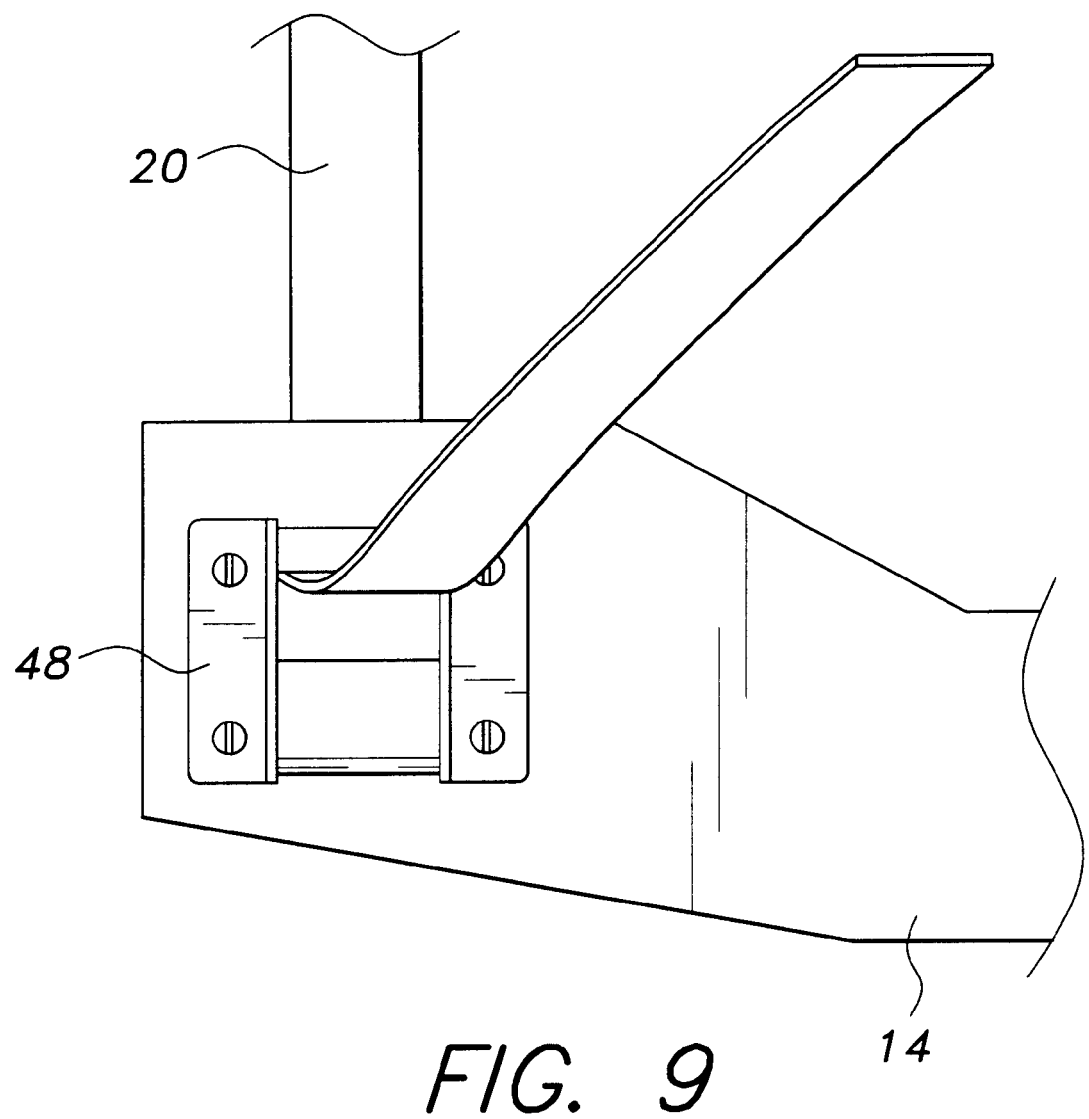
FIG. 9 is a fragmented, perspective view of a straight tension strap inserted through traction applicator slots in a traction applicator having cam-action fastener affixed thereon according to the present invention.

In another form of the invention, shown in FIG. 9, the strap engaging brackets 48 can be affixed to the traction applicator 14 to allow the straight straps 20 to be fastened directly to the traction applicator 14.

Figure 10:
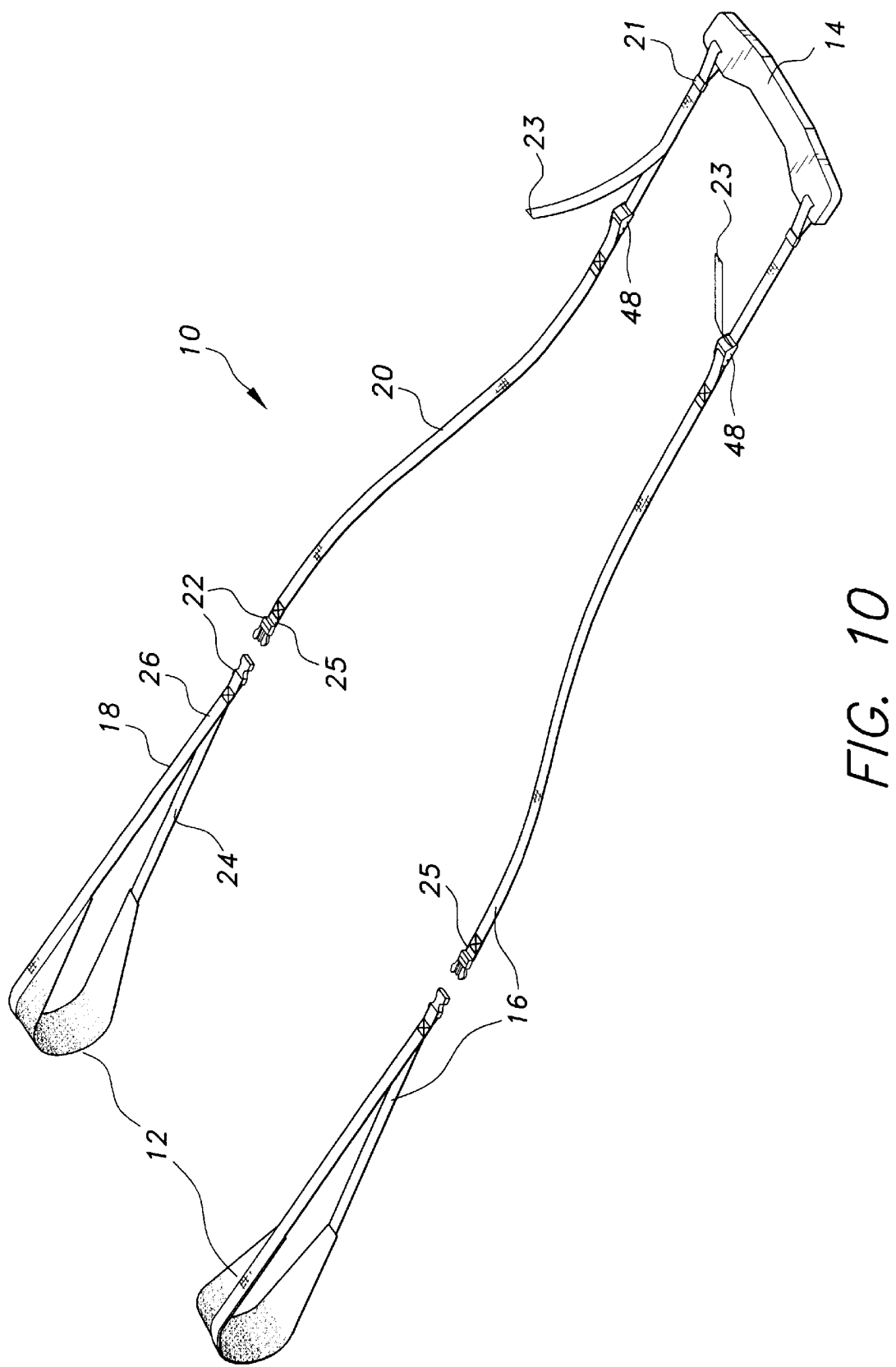
FIG. 10 is a perspective view of a cervical traction device having a straight strap directly attached to a traction applicators according to the present invention.

In yet another form of the invention, shown in FIG. 10, the strap engaging brackets 48 are affixed to the straight tension straps 20. Each straight tension strap 20 is looped through strap slots 36 in the traction applicator 14 and secured at a desired length by the strap engaging brackets 48.

It is to be understood that the present invention is not limited to the embodiments described above, but encompasses any and all embodiments within the scope of the following claims.

We claim:

1. A cervical traction device for applying traction to a patient's shoulder, the patient lying supine on a horizontal support surface, the traction device comprising:
    a rigid substantially rectangular traction applicator, having opposing top and bottom ends connected by and extending between parallel, opposing right and left sides;
    a tension strap assembly having a first tension strap and a second tension strap, each of the tension straps having a looped tension strap and a straight tension strap, each of the straight tension straps having a first end connected to the corresponding looped tension strap and a second end attached to one of the sides of the traction applicator, respectively, so that the first and second straps are spaced apart, the looped tension straps having an inner surface, the looped tension straps being dimensioned and configured for looping around the patient's shoulders; and
    a pair of shoulder pads attached to the inner surface of the looped tension straps;
    wherein the tension straps are adapted for extending from the patient's shoulders past a foot end of the horizontal support surface with the traction applicator depending from the foot end, whereby the patient's shoulders are depressed caudally by applying downward pressure to the traction applicator.

2. The cervical traction device of claim 1, wherein said first and second tension straps each have the straight tension strap and the looped tension strap made from one piece.

3. The cervical traction device of claim 1, said first and second tension straps each further comprise a releasable fastener connecting the looped tension strap to the straight tension strap.

4. The cervical traction device of claim 3, wherein said releasable fastener comprises a quick release buckle.

5. The cervical traction device of claim 1, wherein said tension straps are made from nylon webbing.

6. The cervical traction device of claim 1, wherein said shoulder pads are attached to said inner surface by adhesives.

7. The cervical traction device of claim 1, wherein said shoulder pads are triangular in shape.

8. The cervical traction device of claim 1, wherein said shoulder pads are made from rubber.

9. The cervical traction device of claim 1, wherein said shoulder pads are made from synthetic rubber.

10. The cervical traction device of claim 1, wherein the sides of said traction applicator each have a strap slot defined therein, the traction device further comprising first and second strap engaging brackets attached to said first and second tension straps, respectively, for length adjustment of said tension straps, the second end of the straight tension straps being looped through the strap slots and secured in place by said strap engaging brackets.

11. The cervical traction device of claim 10, wherein said strap engaging brackets comprise cam-action fasteners.

12. The cervical traction device of claim 1, wherein said traction applicator is made from wood.

13. The cervical traction device of claim 1, wherein said traction applicator is made from molded plastic.

14. The cervical traction device of claim 1, wherein said traction applicator is made from aluminum.

15. The cervical traction device of claim 1, wherein said traction applicator has a recess defined along the top end centered between the right and left sides, the recess being dimensioned and configured for receiving a human foot, whereby the patient's shoulders are depressed caudally when a downward pressure is applied to said traction applicator by a human foot.

16. The cervical traction device of claim 1, further comprising a sandbag attached to said traction applicator, whereby the patient's shoulders are depressed caudally by a downward pressure exerted by said sandbag.

17. A method of using a cervical traction device for applying traction to a patient's shoulders, the patient lying supine on a horizontal support surface, the method comprising the steps of:
    positioning a pair of looped tension straps over the patient's shoulders;
    arranging a pair of straight tension straps which extend between the looped tension straps and a traction applicator so that the straight tension straps extend from the patient's shoulders past a foot end of the horizontal support surface with the traction applicator depending from the foot end; and
    applying downward pressure to the traction applicator for depressing the patient's shoulders caudally.

* * * * *